US007112330B1

(12) United States Patent
Buonamassa et al.

(10) Patent No.: US 7,112,330 B1
(45) Date of Patent: Sep. 26, 2006

(54) METHOD FOR PRODUCING YEAST EXPRESSED HPV TYPES 6 AND 16 CAPSID PROTEINS

(75) Inventors: Daniela Tornese Buonamassa, Siena (IT); Catherine E. Greer, Oakland, CA (US); Cesira L. Galeotti, Montegriggioni (IT); Giuliano Bensi, Firenze (IT); Roberto Petracca, Siena (IT)

(73) Assignee: Chiron Corporation, Emeryville, CA (US)

( * ) Notice: Subject to any disclaimer, the term of this patent is extended or adjusted under 35 U.S.C. 154(b) by 0 days.

(21) Appl. No.: 09/762,762

(22) PCT Filed: Aug. 13, 1999

(86) PCT No.: PCT/US99/18016

§ 371 (c)(1),
(2), (4) Date: Apr. 9, 2001

(87) PCT Pub. No.: WO00/09699

PCT Pub. Date: Feb. 24, 2000

Related U.S. Application Data

(60) Provisional application No. 60/096,625, filed on Aug. 14, 1998.

(51) Int. Cl.
*A61K 39/12* (2006.01)

(52) U.S. Cl. ............... 424/204.1; 435/69.1; 435/235.1

(58) Field of Classification Search ............. 424/204.1; 435/69.1, 235.1
See application file for complete search history.

(56) References Cited

U.S. PATENT DOCUMENTS 5,855,891 A * 1/1999 Lowy et al. ............. 424/192.1

FOREIGN PATENT DOCUMENTS

WO   WO 96/05293   2/1996
WO   WO 98/14564   4/1998

OTHER PUBLICATIONS

Sasagawa et al. Virology, 1995, vol. 206, pp. 126-135.*
Buonamassa et al., "Expression of HPV 6 and 16 Capsid Proteins in Yeast and Induction of Specific IgA Response in Mice," *Virus Research*,47(2):126, (1997).
Bonnez et al., "Propagation of Human Papillomavirus Type 11 in Human Xenografts Using the Severe Combined Immunodeficiency (SCID) Mouse and Comparison to the Nude Mouse Model", Virology, (1993) 197:455-458.
Bonnez et al., "Isolation and Propagation of Human Papillomavirus Type 16 in Human Xenografts Implanted in the Severe Combined Immunodeficiency Mouse", J. Virol., (Jun. 1998) 72(6):5256-5261.

Chan et al., "Phylogenetic Analysis of 48 Papillomavirus Types and 28 Subtypes and Variants: A Showcase for the Molecular Evolution of DNA Viruses", J. Virol., (Oct. 1992) 66(10):5714-5725.
Chang et al., "Phenotypic Mixing Between Different Hepadnavirus Nucleocapsid Proteins Reveals C Protein Dimerization To Be Cis Preferential", J. Virol., (Aug. 1994) 68(8):5225-5231.
Christensen et al., "Antibody-Mediated Neutralization In Vivo of Infectious Papillomaviruses", J. Virol., (Jul. 1990) 64(7):3151-3156.
Christensen et al., "Monoclonal Antibody-Mediated Neutralization of Infectious Human Papillomavirus Type 11", (1990) 64(11):5678-5681.
Christensen et al., "Human Papillomavirus Types 6 and 11 Have Antigenically Distinct Strongly Immunogenic Conformationally Dependent Neutralizing Epitopes", Virology, (1994) 205:329-335.
Christensen et al., "Monoclonal Antibodies to HPV-6 L1 Virus-like Particles Identify Conformational and Linear Neutralizing Epitopes on HPV-11 in Addition to Type-Specific Epitopes on HPV-6", Virology, (1996) 224:477-486.
Christensen et al., "Surface Conformational and Linear Epitopes on HPV-16 and HPV-18 L1 Virus-like Particles as Defined by Monoclonal Antibodies", Virology, (1996) 223:174-184.
Deminie et al., "Incorporation of Human Immunodeficiency Virus Type 1 Gag Proteins into Mufine Leukemia Virus Virions", J. Virol., (1993) 67(11):6499-6506.
Doorbar et al., "Identification of Proteins Encoded by the L1 and L2 Open Reading Frames of Human Papillomavirus 1A", J. Virol., (Sep. 1987) 61(9):2793-2799.
Firzlaff et al., "Detection of Human Papillomavirus Capsid Antigens in Various Squamous Epithelial Lesions Using Antibodies Directed Against the L1 and L2 Open Reading Frames", Virology, 164:467-477.
Franke et al., "Specificity and Sequence Requirements for Interactions Between Various Retroviral Gag Proteins", J. Virol., (Aug. 1994) 68(8):5300-5305.
Greer et al., "Human Papillomavirus (HPV) Type Distribution and Serological Response to HPV Type 6 Virus-Like Particles in Patients with Genital Warts" (Aug. 1995) J. Clinical Microbiology 33(8):2058-2063.
Hagensee et al., "Self-Assembly of Human Papillomavirus Type 1 Capsids by Expression of L1 Protein Alone or by CoExpression of the L1 and L2 Capsid Proteins", J. Virol., (Jan. 1993) 67(1):315-322.
Hagensee et al., "Three-Dimensional Structure of Vaccinia Virus-Produced Human Papillo mavirus Type 1 Capsids", J. of Virol., (Jul. 1994) 68(7):4503-4505.
Hines et al., "The Expression and Processing of Human Beta-Amyloid Peptide Precursors in *Saccharomyces cerevisae*: Evidence for a Novel Endopeptidase in the Yeast Secretory System", Cell. Mol. Biol. Res., (1994) 40(4):273-284.

(Continued)

*Primary Examiner*—Ali R. Salimi
(74) *Attorney, Agent, or Firm*—Rececca M. Hale; Roberta L. Robins; Alisa A. Harbin

(57) ABSTRACT

Mosaic VLPs of viral capsid proteins from different virus types are described, as are methods of making the same. Specifically, a diploid yeast strain that coexpresses the L1 and L2 capsid proteins of both HPV-6 and HPV-16 as mosaic VLPs is described. The mosaic VLPs induced the production conformational antibodies against both L1 proteins upon administration to mice.

17 Claims, 8 Drawing Sheets

OTHER PUBLICATIONS

Hofmann et al., "Sequence Determination of Human Papillomavirus 6A and Assembly of Virus-like Particles in *Saccharomyces cerevisae*", Virology, (1995) 209:506-518.

Hofmann et al., "Sequence Conservation Within the Major Capsid Protein of Human Papillomavirus (HPV) Type 18 and Formation of HPV-18 Virus-like Particles in *Saccharomyces cerevisiae*", J. Gen. Virol., (1996) 77:465-468.

Jansen et al., "Vaccination with Yeast-Expressed Cottontail Rabbit Papillomavirus (CRPV) Virus-like Particles Protects Rabbits from CRPV-Induced Papilloma Formation", Vaccine, (1995) 13(16):1509-1514.

Kirnbauer et al., "Papillomavirus L1 Major Capsid Protein Self-Assembles Into Virus-like Particles That Are Highly Immunogenic", Proc. Natl. Acad. Sci. USA, (1992) 89:12180-12184.

Kirnbauer et al., "Efficient Self-Assembly of Human Papillomavirus Type 16 L1 and L1-L2 Into Virus-like Particles", J. Virol., (1993) 67(12):6929-6936.

Kirnbauer et al., "Virus-Like Particles of Bovine Papillomavirus Type 4 In Prophylactic and Therapeutic Immunization", Virology, (1996) 219:37-44.

Kreider et al., "Laboratory Production In Vivo of Infectious Human Papillomavirus Type 11", (1 J. Virol., (Feb. 1987) 61(2):590-593.

Li et al., "Expression of the Human Papillomavirus Type 11 L1 Capsid Protein in *Escherichia coli*: Characterization of Protein Domains Involved in DNA Binding and Capsid Assembly", J. Virol., (Apr. 1997) 71(4):2988-2995.

Li et al., "Intercapsomeric Disulfide Bonds in Papillomavirus Assembly and Disassembly", J. Virol., (Mar. 1998) 72(3):2160-2167.

Lowe et al., "Human Papillomavirus Type 11 (HPV-11) Neutralizing Antibodies in the Serum and Genital Mucosal Secretions of African Green Monkeys Immunized with HPV-11 Virus-like Particles Expressed in Yeast", J. Infect. Dis., (1997) 176:1141-1145.

Muller et al., "Papillomavirus Capsid Binding and Uptake by Cells from Different Tissues and Species", J. Virol., (Feb. 1995) 69(2):948-954.

Neeper et al., "Expression of the Major Capsid Protein of Human Papillomavirus Type 11 in *Saccharomyces cerevisae*", Gene, (1996) 180:1-6.

Ott et al., Design and Evaluation of a Safe and Potent Adjuvant for Human Vaccines (1995) in M.F. Powell and M. J. Newman (ed.), Vaccine Design., The subunit and adjuvant approach. (1995) 277-296 Plenum Press, New York, N.Y.

Qi et al., "Epithelial Cells Display Separate Receptors for Papillomavirus VLPs and for Soluble L1 Capsid Protein", Virology, (1996) 216:35-45.

Roden et al., "Neutralization of Bovine Papillomavirus by Antibodies to L1 and L2 Capsid Proteins", J. Virol., (Nov. 1997) 68(11):7570-7574.

Roden et al., "Interaction of Papillomaviruses with the Cell Surface", J. Virol., (Nov. 1994) 68(11):7260-7266.

Roden et al., "In Vitro Generation and Type-Specific Neutralization of a Human Papillomavirus Type 16 Virion Pseudotype", J. Virol., (Sep. 1996) 70(9):5875-5883.

Roden et al., "Assessment of Serological Relatedness of Genital Human Papillomavirus by Hemagglutination Inhibition", J. Virol., (May 1996) 70(5):3298-3301.

Rose et al., "Serological Differentiation of Human Papillomavirus Types 11, 16, and 18 Using Recombinant Virus-Like Particles", J. Gen. Virol., (1994) 75:2445-2449.

Rose et al., "Expression of Human Papillomavirus Type 11 L1 Protein in Insect Cells: In Vivo and In Vitro Assembly of Virus-like Particles", J. Virol., (Apr. 1993) 67(4):1936-1944.

Sapp et al., "Organization of the Major and Minor Capsid Proteins in Human Papillomavirus Type 33 Virus-like Particles", J. Gen. Virol., 76: 2407-2412.

Sapp et al., "Papillomavirus Assembly Requires Trimerization of the Major Capsid Protein by Disulfides Between Two Highly Conserved Cysteines", J. Virol., (Jul. 1998) 72 (7):6186-6189.

Smith et al., "Titration of HPV-11 Infectivity and Antibody Neutralization Can Be Measured In Vitro.", (1995) J. Invest. Dermatol. 105(3):438-444.

Suzich et al., "Systemic Immunization With Papillomavirus L1 Protein Completely Prevents the Development of Viral Mucosal Papillomas", Proc. Natl. Acad. Sci. USA, (Dec. 1995) 92:1553-1557.

Touze et al., "Production of Recombinant Virus-like Particles From Human Papillomavirus Types 6 and 11, and Study of Serological Reactivities Between HPV 6, 11, 16, and 45 by ELISA: Implications for Papillomavirus Prevention and Detection", FEMS Microbiol., (1998) 160:111-118.

Travis et al., "Isolation and Properties of Recombinant DNA Produced Variants of Human $\alpha_1$ -Proteinase Inhibitor", J. of. Biol. Chem., (1985) 260(7):4384-4389.

Unckell et al., "Generation and Neutralization of Pseudovirions of Human Papillomavirus Type 33", J. Virol., (Apr. 1997) 71(4):2934-2939.

Van Ranst et al., "Phylogenetic Classification of Human Papillomaviruses: Correlation With Clinical Manifestations", J. Gen. Virol., (1992) 73:2653-2660.

Volpers et al., "Assembly of the Major and the Minor Capsid Protein of Human Papillomavirus Type 33 into Virus-like Particles and Tubular Structures in Insect Cells", Virology, (1994) 200:504-512.

Volpers et al., "Binding and Internalization of Human Papillomavirus Type 33 Virus-like Particles by Eukaryotic Cells", J. Virol., (Jun. 1995) 69(6):3258-3264.

White et al., "In Vitro Infection of Type-Restricted Antibody-Mediated Neutralization of Authentic Human Papillomavirus Type 16", J. Virol. (Feb. 1998) 72(2):959-964.

Zaret et al., "$\alpha$-Aminoadipate as a Primary Nitrogen Source for *Saccharomyces cerevisiae* Mutants", J. Bacteriol., (May 1985) 162(2):579-583.

Zavada et al., "The Pseudotypic Paradox", J. Gen. Virol., (1982) 63:15-24.

Zhou et al., "Synthesis and Assembly of Infectious Bovine Papillomavirus Particles In Vitro", J. Gen. Virol., (1993) 74:763-768.

Zimmerman et al., "Procedures Used in the Induction of Mitotic Recombination and Mutation in the Yeast *Saccharomyces cerevisiae*", Mutat. Res., (1975) 31:71-86.

Notice of Opposition to a European Patent, Patent No. EP 1 105 495, "Method for Producing Yeast Expressed HOV Types 6 and 16 Capsid Proteins," Chiron Corporation, EPA Form 2300.1 04.93. Total pp. 7, Mar. 16, 2005.

\* cited by examiner

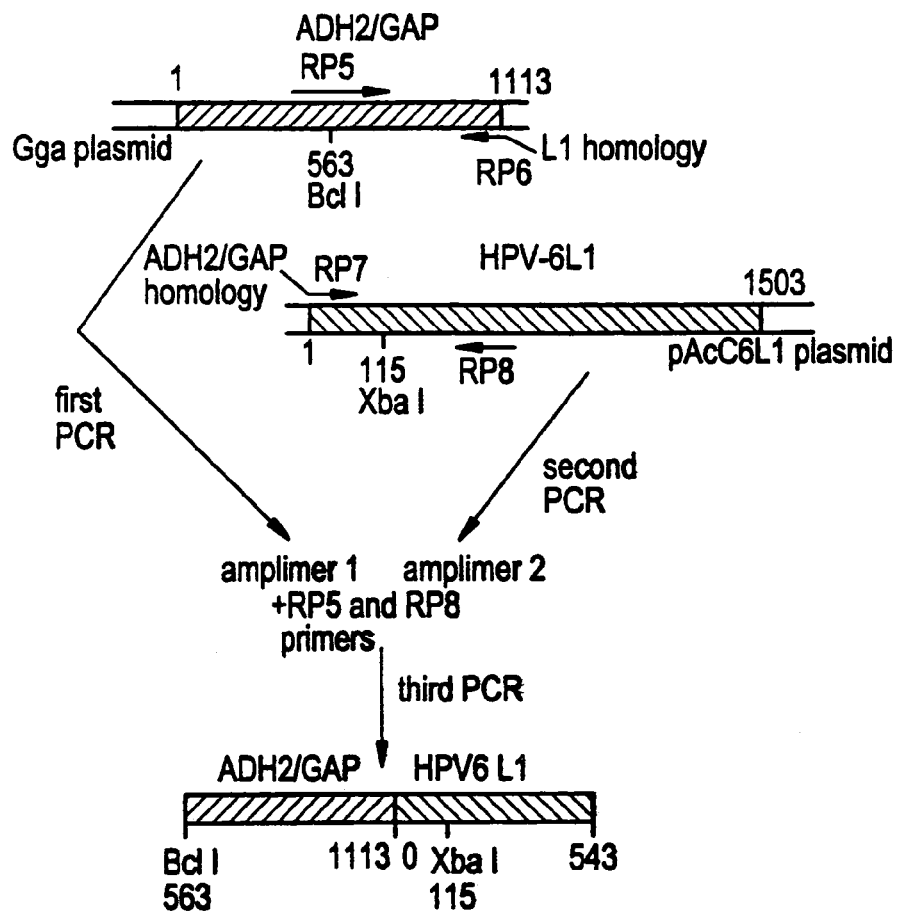
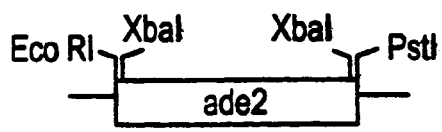
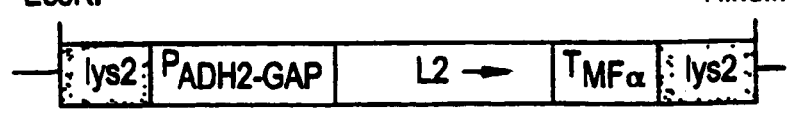

anti-L1
1 2 3 anti-HPV-6
antibodies

-68
-43
-29 anti-L2
1 2 3 anti-HPV-6
antibodies

-113
-75
-48 anti-L1
1 2 3 anti-HPV-16
antibodies

-68
-43
-29 anti-L2
1 2 3 anti-HPV-16
antibodies

-113
-75
-48

SEQUENCE LISTING

```
<160> NUMBER OF SEQ ID NOS: 13

<210> SEQ ID NO 1
<211> LENGTH: 36
<212> TYPE: DNA
<213> ORGANISM: Artificial
<220> FEATURE:
<223> OTHER INFORMATION: primer

<400> SEQUENCE: 1
actgatagtt tgatcaaagg ggcaaaacgt aggggc                           36

<210> SEQ ID NO 2
<211> LENGTH: 36
<212> TYPE: DNA
<213> ORGANISM: Artificial
<220> FEATURE:
<223> OTHER INFORMATION: primer

<400> SEQUENCE: 2
gtcgctaggc cgccacatgg tgtttgttta tgtgtg                           36

<210> SEQ ID NO 3
```

```
<211> LENGTH: 36
<212> TYPE: DNA
<213> ORGANISM: Artificial
<220> FEATURE:
<223> OTHER INFORMATION: primer

<400> SEQUENCE: 3
aaacacacat aaacaaacac catgtggcgg cctagc                         36

<210> SEQ ID NO 4
<211> LENGTH: 36
<212> TYPE: DNA
<213> ORGANISM: Artificial
<220> FEATURE:
<223> OTHER INFORMATION: primer

<400> SEQUENCE: 4
gcagtcacca ccctgtacag gtgtattagt acactg                         36

<210> SEQ ID NO 5
<211> LENGTH: 31
<212> TYPE: DNA
<213> ORGANISM: Artificial
<220> FEATURE:
<223> OTHER INFORMATION: primer

<400> SEQUENCE: 5
gcggcgaatt ctagaacagt tggtatatta g                              31

<210> SEQ ID NO 6
<211> LENGTH: 33
<212> TYPE: DNA
<213> ORGANISM: Artificial
<220> FEATURE:
<223> OTHER INFORMATION: primer

<400> SEQUENCE: 6
gcggcctgca gggtctagac tcttttccat ata                            33

<210> SEQ ID NO 7
<211> LENGTH: 23
<212> TYPE: DNA
<213> ORGANISM: Artificial
<220> FEATURE:
<223> OTHER INFORMATION: primer

<400> SEQUENCE: 7
gcggaattcc actagtaatt aca                                       23

<210> SEQ ID NO 8
<211> LENGTH: 22
<212> TYPE: DNA
<213> ORGANISM: Artificial
<220> FEATURE:
<223> OTHER INFORMATION: primer

<400> SEQUENCE: 8
gatgtaagct tctactagtt ga                                        22

<210> SEQ ID NO 9
<211> LENGTH: 19
<212> TYPE: DNA
<213> ORGANISM: Artificial
<220> FEATURE:
<223> OTHER INFORMATION: primer

<400> SEQUENCE: 9
```

```
cgacacaaac gttctgcaa                                           19

<210> SEQ ID NO 10
<211> LENGTH: 30
<212> TYPE: DNA
<213> ORGANISM: Artificial
<220> FEATURE:
<223> OTHER INFORMATION: primer

<400> SEQUENCE: 10
attagtcgac ctaggcagcc aagagacatc                               30

<210> SEQ ID NO 11
<211> LENGTH: 24
<212> TYPE: DNA
<213> ORGANISM: Artificial
<220> FEATURE:
<223> OTHER INFORMATION: primer

<400> SEQUENCE: 11
tctcttggct gcctagtgag gcca                                     24

<210> SEQ ID NO 12
<211> LENGTH: 35
<212> TYPE: DNA
<213> ORGANISM: Artificial
<220> FEATURE:
<223> OTHER INFORMATION: primer

<400> SEQUENCE: 12
ctagtaatgt cgacttacag cttacgtttt ttgcg                         35

<210> SEQ ID NO 13
<211> LENGTH: 17
<212> TYPE: DNA
<213> ORGANISM: Artificial
<220> FEATURE:
<223> OTHER INFORMATION: primer

<400> SEQUENCE: 13
tagttttaaa acaccaa                                             17
```

METHOD FOR PRODUCING YEAST EXPRESSED HPV TYPES 6 AND 16 CAPSID PROTEINS

CROSS-REFERENCE TO RELATED APPLICATIONS

The present application is a 35 U.S.C. §317 filing of PCT/US99/18016, filed Aug. 13, 1999, which claims the benefit under 35 U.S.C. § 119(e) to Provisional Application Ser. No. 60/096,625, filed Aug. 14, 1998. The foregoing applications are incorporated by reference herein in their entireties.

FIELD OF THE INVENTION

The present invention is related to the production of mosaic virus-like particles comprising capsid proteins of human papilloma virus (HPV) types 6 and 16 capable of inducing immune response against both HPV types.

BACKGROUND OF THE INVENTION

A promising strategy to induce an immune response capable of neutralizing papillomavirus (PV) infections is the use of virus capsid proteins as antigens. In the case of genital human papillomaviruses (HPVs), this approach was hampered by the lack of any in vivo or in vitro source of sufficient amounts of native virus. In order to overcome this problem, heterologous expression systems have been extensively used to obtain large quantities of capsid proteins and to allow the analysis of their structural and immunological properties. Expression of the major capsid protein late 1 (L1) from different PV types using prokaryotic (25), baculovirus (21, 23, 37, 41, 42, 46), yeast (14, 18, 19, 20, 29) and mammalian expression system (15, 16, 51), demonstrated that this protein can self-assemble into virus-like particles (VLPs). Coexpression of the minor capsid protein late 2 (L2) is not strictly necessary to obtain VLPs, although its presence increases the efficiency of particle formation (15, 22, 51) and induces anti-L2 neutralizing antibodies (32) The L1 and L2 VLPs appear similar to native virions by electron microscopy (EM). The use of different animal models has shown that VLPs can be very efficient at inducing a protective immune response.

VLPs meet many of the criteria which make them ideal surrogates of native virions. They resemble infectious particles by ultrastructural analysis (16), elicit virus neutralizing antibodies and bind to the putative receptor on the surface of mammalian cells (28, 31, 33, 44, 47). Most notably, the results obtained with animal models demonstrated that prophylactic immunization with VLPs can be very effective in vivo. Cottontail rabbits, calves and dogs immunized with L1 VLPs were protected from subsequent challenge with the homologous PV (20, 23, 41) and passive transfer of immune sera conferred protection to naive animals (20, 41), indicating that an antibody-mediated response plays a major role in preventing virus infection.

Studies with infectious HPV virions, as well as VLPs of different HPV types, strongly suggested, however, that the immune response is predominantly type-specific. Further, the efficacy of VLP-based anti-HPV vaccine candidates cannot be evaluated in animals since these viruses exhibit a high degree of species specificity. Antibody-mediated virus neutralization has been therefore studied using either in vitro assays (35, 40) or xenograft systems which allow propagation of infectious virus of specific HPV types (1, 2, 5, 6, 24). The primary conclusion which could be drawn from these experiments was that immunization with HPV VLPs evokes a neutralizing immune response which is predominantly type-specific (6, 7, 34, 35, 36, 48).

Cross-neutralization has been reported between HPV-6 and HPV-11 (92% amino acid sequence identity) (8) and between HPV-16 and HPV-33 (80% amino acid sequence identity) (48). This may indicate the existence of some correlation between protein sequences and structural similarities that could possibly be relevant for the mechanism of capsid assembly. On the basis of these considerations, however, the concept that HPV-6 and HPV-16 L1 proteins may coassemble is not obvious, since the two viruses belong to phylogenetically more distant groups (3, 45) and exhibit a lower (67%) L1 amino acid sequence identity.

Further, while envelope proteins of viruses belonging to very different families can be incorporated into the same envelope (50), nucleocapsid protein mixing appears to be much more restricted. Mixed core particles between Moloney murine leukemia virus (MuLV) and human immunodeficiency virus (HIV) have been obtained but only when artificial chimeric Gag precursors, containing both UV and MuLV determinants are coexpressed with wild-type MuLV Gag proteins (10). By using a yeast two-hybrid system based on GAL4-Gag fusion protein expression plasmids, Franke et al. were able to show that the ability of two heterologous Gag proteins to multimerize was correlated with the genetic relatedness between them (13).

Mixed capsid formation between wild-type Gag proteins has not been reported so far. In the case of the hepadnavirus core (C) protein, Chang et al. (4) have shown that an epitope-tagged truncated hepatitis B virus (HBV) C polypeptide could coassemble in *Xenopus* oocytes with woodchuck hepatitis virus (WHV) and ground squirrel hepatitis virus (GSHV) C proteins but not with that of duck hepatitis B virus (DHBV). This result was not unexpected since the two core protein sequences have diverged significantly and do not show immunological cross-reactivity. When coassembly of C polypeptides of HBV, WHV and GSHV occurred, formation of mixed capsids resulted from the aggregation of different species of homodimers (4).

Several reports have discussed the importance of disulfide bonds for the integrity of native bovine papillomavirus type 1 (HPV-1) virions (26) and VLP structure (25, 38, 39). L1 et al. (26) have also shown that the cysteine 424 mutant (C424) of HPV-11 L1 in the carboxy-terminal domain that has been identified as critical for capsid formation (25), is still able to form capsomeres but not VLPs, indicating that this residue may be involved in interpentamer bonding. The essential role of disulfide bonds has been confirmed by a single point mutation of either C176 or C427 in HPV-33 L1 (C428 in HPV-18 L1), which converts all VLP trimers into monomers, allowing capsomere formation but not VLP assembly (39).

It has been recently proved that, by using an in vitro infection system and a sensitive reverse transcriptase PCR-based assay (RT-PCR), antisera to HPV-6 VLPs are not able to neutralize authentic HPV-16 virions (48). Since cysteine residues corresponding to those described as involved in disulfide bonding above are conserved in the HPV-6 and HPV-16 L1 proteins, we hypothesized that mosaic VLPs could either result from intra-capsomeric or intercapsomeric association of the two proteins and/or from interaction between type-specific subsets of capsomeres.

SUMMARY OF THE INVENTION

In one aspect, the present invention relates to a method for producing mosaic virus like particles comprising the capsid proteins from at least two types of viruses, preferably animal, more preferably HPV. In a preferred aspect, the capsid proteins are from HPV types 6 and 16. In a further preferred aspect, the capsid proteins are L1 and L2 from HPV types 6 and 16.

In a further aspect, the present invention relates to vectors and hosts for expressing the capsid proteins of at least two types of viruses, preferably animal, more preferably HPV. In a preferred aspect, the capsid proteins are from HPV types 6 and 16. In a further preferred aspect, the capsid proteins are L1 and L2 from HPV types 6 and 16. In a further preferred aspect, the present invention relates to a diploid yeast strain that coexpresses the L1 and L2 capsid proteins of HPV-6 and HPV-16 as mosaic VLPs.

In another aspect, the present invention relates to a method for inducing an immune response against more than one type of virus using mosaic VLPs comprising capsid proteins from each virus type. In a preferred aspect, the mosaic VLPs comprise capsid proteins from animal viruses, more preferably HPV, most preferably HPV types 6 and 16. In a further preferred aspect, the mosaic VLPs comprise the L1 and L2 capsid proteins from HPV types 6 and 16.

In still another aspect, the present invention relates to an immunogenic virus like particle comprising capsid proteins from different types of viruses, preferably animal, more preferably HPV, most preferably HPV types 6 and 16. In a further preferred aspect, the mosaic VLPs comprise the L1 and 12 capsid proteins from HPV types 6 and 16.

BRIEF DESCRIPTION OF THE DRAWINGS

FIG. 2 depicts the recombinant PCR performed in constructing the pBS-6L1 plasmid.

FIG. 4 is a schematic representation of the yeast integrative plasmids YIpAde (a) and YIpLys-L2 (b) vectors. The continuous lines represent pUC vector sequences. The empty box in (a) represents the adenine 2 gene sequence. The black boxes in (b) represent lysine 2 gene fragments, the grey box represents the L2 gene, the empty boxes represent the ADH2/GAP hybrid promoter and the MFα gene transcriptional termination sequence. The arrow in the L2 box indicates the 5'-3' orientation of the coding sequence. Relevant restriction sites are indicated

DETAILED DESCRIPTION OF THE INVENTION

Figure 1:
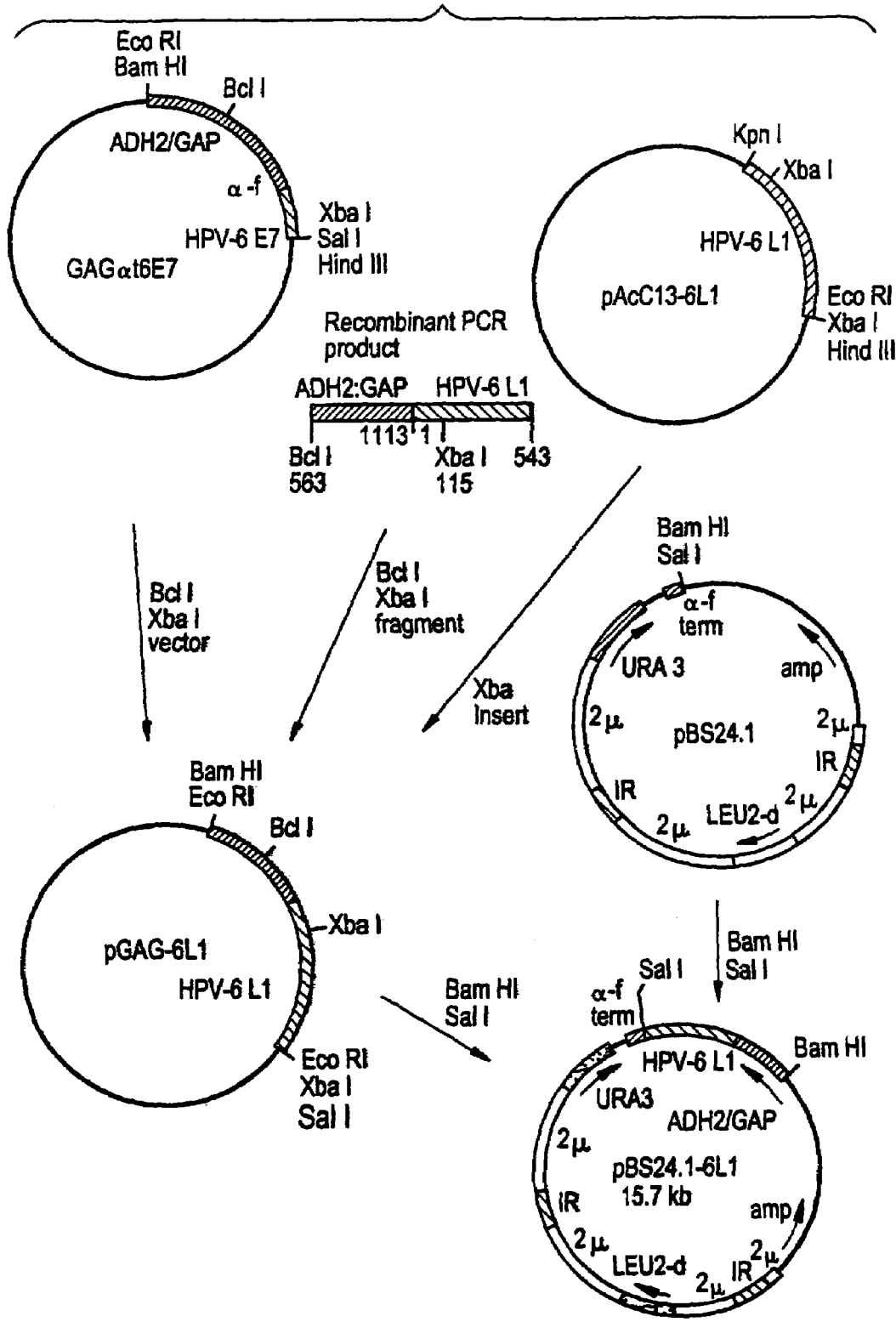
FIG. 1 is a schematic of the construction of the pBS-6L1 plasmid.
Figure 3A:
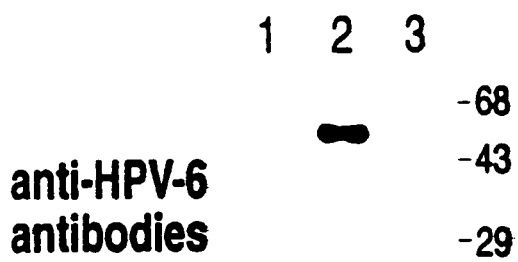
FIG. 3 depicts a Western blot analysis of cell exam from yeast strains expressing HPV-6 and HPV-16 capsid proteins. Equivalent amounts of total cell extracts from the parental JSC310 strain (lanes 1) and different recombinant strains (lanes 2 and 3) were separated by 10% SDS-PAGE, electrotransferred to nitrocellulose filters and incubated with the H6.C6 (a) or the H16.H5 (c) type-specific anti-L1 Mabs, and with HPV6L2 (b) or HPV-16L2 (d) antisera Lanes 2a and 2c: JSC30-6L1 epi; lanes 3a and 3c: JSC310-16L1 epi; lanes 2b and 2d: JSC310-6L2epi; lanes 3b and 3d: JSC310-16L2epi. Molecular mass standards (in kDa) are indicated. This multipanel figure and those which follow have been assembled by using Photoshop 4.0 and FreeHand 7.0 programs for Macintosh.
Figure 3B:
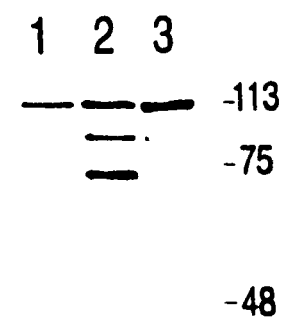
Figure 3C:
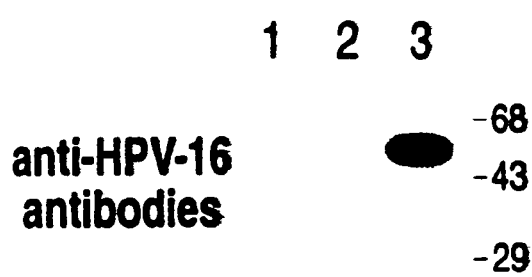
Figure 3D:
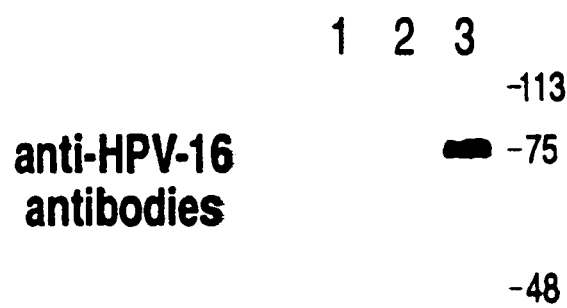
Figure 5A:
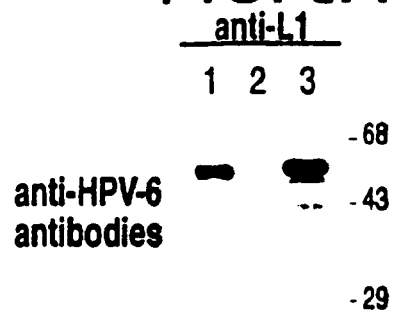
FIG. 5 depicts a Western blot analysis of cellular from recombinant haploid and diploid yeast strains Total cell extracts were separated by 10% SDS-PAGE, electrotransferred to nitrocellulose filters and incubated with anti-HPV-6 L1 (a) and anti-HPV-16 L1 (c) Mabs and with HPV-6 L2 (b) and HPV-16 L2 (d) antisera. Lanes 1: AB110-6L1/16L2; lanes 2: JSC310-16L1/6L2; lanes 3: AB/JS-4L; lanes 4: JSC310-6L2epi; lanes 5: JSC310-16L2epi Arrows in (b) and (d) indicate the bands corresponding to the L2 proteins. Molecular mass standards (in kDa) are indicated.
Figure 5B:
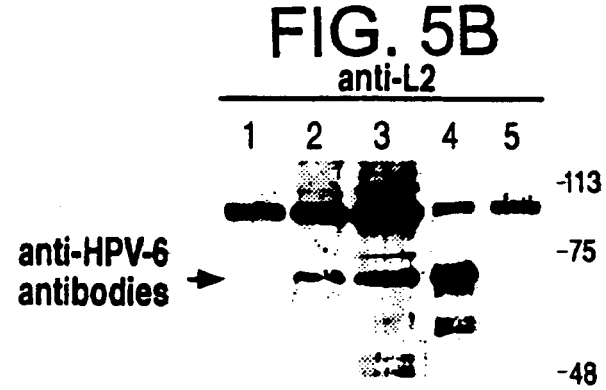
Figure 5C:
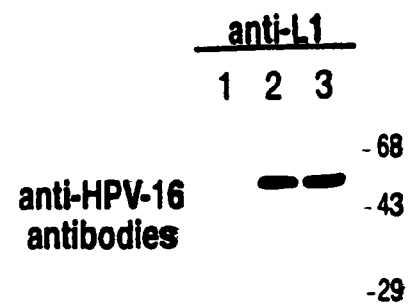
Figure 5D:

To test the possibility of inducing antibodies against multiple HPV types, we have generated a recombinant yeast diploid strain that comprises the HPV-6 and HPV-16 L1 and L2 genes. HPV-6/16 mosaic VLPs were purified from the cell lysate and used as antigens to immunize mice. The data presented below supports the formation of mosaic VLPs comprising all four proteins. The immunoprecipitation experiment strongly suggests that the CsCl purified VLPs represent the result of a reciprocal interaction of the two L1 proteins, rather than the simple coexistence of different VLP types. The fact that the L2 proteins are present in the same CsCl fractions favors the hypothesis that they are incorporated into the VLPs as well, since the L2 protein alone does not band in a CsCl gradient at the same density as L1 VLPs (22). Further, antisera able to recognize conformational somal expression vector pBS24.1. Expression of the HPV-6 and HPV-16 L2 proteins was instead obtained by cloning the expression cassette into an integrative plasmid suitable for insertion into the lys2 locus of the haploid strain genome (FIG. 4b). As a consequence of this cloning strategy, the L1 and L2 gene copy numbers in the haploid strains were different and this resulted in higher expression levels of the L1 proteins. This should resemble the ratio of L1 to L2 observed in native HPV virions, which has been estimated over a range from 5:1 to 30:1 (25). Table lists the parental yeast strains used, the two recombinant haploid strains obtained and the diploid strain resulting from the mating.

TABLE 1

List of parental and recombinant yeast strains with genotypes and HPV expressed genes

| Yeast strain | Genotype | Episomal HPV gene | Integrated HPV gene |
|---|---|---|---|
| JSC310 | MATa leu2-3 ura3-52 prb1-1122 pep4-3 prc1-407 adr1::DM15 cir°. | | |
| AB110 | MATa leu2-3-112 ura3-52 pep4-3 his4-580 cir° | | |
| JSC310-6L1epi | MATa prb1-1122 pep4-3 prc1-407 adr1::DM15 cir° | 6L1 | |
| JSC310-16L1epi | MATa prb1-1122 pep4-3 prc1-407 adr1::DM15 cir° | 16L1 | |
| JSC310-6L2epi | MATa prb1-1122 pep4-3 prc1-407 adr1::DM15 cir° | 6L2 | |
| JSC310-16L2epi | MATa prb1-1122 pep4-3 prc1-407 adr1::DM15 cir° | 16L2 | |
| JSC310-6L2int 6L2 | MATa leu2-3 ura3-52 prb1-1122 lys2 pep4-3 prc1-407 adr1::DM15 cir° | | |
| AB110-16L2int | MATa leu2-3-112 ura3-52 pep4-3 lys2 his4-580 cir° | | 16L2 |
| JSC310-16L1/6L2 6L2 | MATa prb1-1122 lys2 prc1-407 pep4-3 ade2 adr1::DM15 cir° | 16L1 | |
| AB110-6L1/16L2 | MATa pep4-3 lys2 his4-580 cir° | 6L1 | 16L2 |
| AB/JSC-4L 16L2 | MATa/MATa PRB1/prb1-1122 lys2/lys2 PRC1/prc1-407 pep4-3/pep4-3 HIS4/his4-580 ADR1/adr1::DM15 cir° | 6L1–16L1 | 6L2– | epitopes of both L1 proteins were obtained. Although it remains to be confirmed that the immune response elicited by HPV-6/16 VLPs can neutralize the two viruses, the data herein supports using mosaic VLPs to immunize against a broader spectrum of virus types.

A yeast expression system as herein disclosed is preferred. Different laboratories have observed that a Saccharomyces cerevisiae expression system can be successfully used to easily purify PV VLPs (14, 18) which are highly efficient at inducing a protective immune response in animal models (20). Yeast-expressed VLPs are able to elicite a specific immune response not only at systemic but also at mucosal level. Lowe et al. have reported the generation of IgG neutralizing antibodies in the sera and gal secretions of African green monkeys immunized intramuscularly with HPV-11 VLPs, adsorbed to aluminum adjuvant (27). Greer et al. have observed the induction of anti-L1 specific IgG and IgA antibodies in the sera and genital secretions of mice immunized intranasally with HPV6 VLPs, adjuvanted either with E. coli heat-labile enterotoxin (LT) or with a LT-derived non toxic mutant (14). Further, yeast expression affords the potential to scale-up to thousands of liters at relatively low cost and many yeast-derived products for human use are already market approved due to their safety.

To express the HPV6 and HPV-16 L1 and l2 genes in the same yeast cell, we generated a S. cerevisiae diploid stain by mating two haploid stains, each expressing two of the four capsid proteins. In order to obtain expression of the heterologous genes under identical culture conditions, each of them was cloned into the same expression cassette based on the ADH2/GAP glucose-repressible hybrid promoter and the $T_{MF\alpha}$ transcriptional termination sequence. The HPV-6 and HPV-16 L1 proteins were expressed by means of the epi- As used herein, the term "mosaic VLP" refers to a VLP comprising capsid proteins from more than one type of virus. VLPs which result from intra- and/or inter-capsomeric association of the proteins are included.

As used herein, the term "type" in reference to viruses includes viruses (animal and plant) within the same family, group, or genus as well as viruses in different families, groups, or genuses.

As used herein, the term "non-integrative" in reference to a vector indicates that the vector does not integrate into the host DNA.

Yeast strains. The Saccharomyces cerevisiae haploid strains used were JSC310 (MATa, leu2-3, ura3-52, prb1-1122, pep4-3, prc1-407, adr1::DM15, cir°)(17) and AB110 (MATα, leu2-3-112, ura3-52, pep4-3, his4-580, cir°)(43), provided by Vicky Hines (Chiron Corporation, Emeryville, Calif., USA).

Monoclonal and polyclonal antibodies. The H6.C6 and H16.H5 monoclonal antibodies (Mabs), which bind to denatured HPV-6 and HPV-16 L1 proteins, respectively, in addition to the H6.B10.5 and H16.V5 Mabs, specific for HPV-6 and HPV-16 intact VLPs, have been reported by Christensen et al. (8, 9). For Western blot analysis, these Mabs were used at 1:3000 dilution with a 4° C. overnight incubation. HPV-16 L2 rabbit antiserum was a gift of Lutz Gissmann (DKFZ, Heidelberg, Germany), while HPV-6 L2 rabbit antisera were kindly provided by Denise Galloway (Fred Hutchinson Cancer Research Center Seattle, Wash.) and Robert C. Rose (University of Rochester, N.Y.). All the antisera were used at 1:3000–5000 dilution with a 4° C. overnight incubation. Anti-rabbit and anti-mouse peroxidase-conjugated antibodies were from Biosource International (Camarillo, Calif.) and were used at 1:5000 dilution at room temperature for 1.5 hours.

EXAMPLE 1

HPV Type-Specific Detection of Capsid Proteins Expressed in Yeast.

A single yeast strain which could express the four HPV-6 and HPV-16 L1 and L2 capsid proteins was prepared. A necessary tool in achieving this was the availability of antibodies which reacted specifically or preferentially with the L1 or the L2 protein of only one HPV The HPV-6 and HPV-16 L1 and L2 genes were cloned in the episomal vector pBS24.1 (see Example 2 below) and expressed in the S. cerevisiae strain JSC310 to test the type specificity of the available antibodies. FIG. 3 shows the results of a Western blot analysis of total cell extra prepared from the recombinant strains incubated with specific anti-HPV-6 (a) or HPV-16 (c) L1 Mabs and with HPV-6 (b) or HPV-16 (d) L2 antisera. In all cases HPV type-specific bands were detected, although a weak cross-reactivity could be seen for both the L2 antisera. While the HPV-6 and HPV-16 L1 Mabs identified proteins with the expected molecular weight of about 55 kilodalton (kDa) the L2 proteins, as previously reported (11, 12) showed an electrophoretic mobility corresponding to approximately 72–75 kDa, instead of the 55 kDa predicted on the basis of their amino acid sequences.

EXAMPLE 2

Construction of Recombinant Plasmids

DNA fragments encoding the HPV proteins were obtained from available recombinant plasmids, either by restriction enzyme digestion or by PCR amplification (Expand High Fidelity PCR System, Boehringer Mannheim), and they were completely sequenced using an Applied Biosystem (Norvalk, CELLTECH, USA) model 373 DNA sequencer.

The episomal yeast expression vector pBS24.1, a yeast "shuttle" vector (17 and Philip J. Barr, Chiron Corporation, Emeryville, Calif., USA), containing the leucine 2 (Leu2) and uracil 3 (Ura3) selectable genes was used. In this instance, it was obtained by digesting an available pBS24.1αt6E7 plasmid with Bam HI and Sal I. The pBS24.1αt6E7 plasmid was prepared for the yeast expression of the HPV-6E7 antigen in a secreted form.

The pBS-6L1 plasmid, expressing the HPV4 L1 protein under the control of the alcohol-dehydrogenase-2-glyceraldehyde-3-phosphate-dehydrogenase (ADH2/GAP) glucose repressible promoter (J. Shuster, Chiron Corporation, Emeryville, Calif., USA) and the mating type alpha factor gene transcriptional termination sequence ($T_{MF\alpha}$) was derived from the pBS24.1 plasmid as follows.

The plasmid pBS-6L1 is a yeast expression vector which contains the HPV-6L1 under the control of the ADH2\GAP promoter cloned into BAM HI and Sal I sites of the vector pBS24.1. The vector pBS24.1 contains the α-factor terminator, therefore an "expression cassette" for HPV-6L1 is obtained. The "expression cassette" for HPV-6L1 consists of the following sequences fused together (from 5' to 3'): ADH2\GAP hybrid promoter, HPV-6L1 gene, and α-factor terminator. At the end of the cloning procedures the above expression cassette was obtained into the pBS24.1 (17). The vector pBS24.1 may be replicated both in *Escherichia coil* and in *Saccharomyces cerevisiae* since it contains PBR322 sequences (including the origin of replication and the ampicillin resistance gene) and the complete 2μ sequences (including the origin of replication). It also contains the yeast URA3 gene and the yeast LEU2 gene.

A summary of the construction of plasmid pBS24.1-A/G-6L1 is presented schematically in FIG. 1. Due to the lack of suitable restriction sites, the fusion between the glucose repressible ADH2\GAP promoter and the L1 ORF has been obtained by means of recombinant PCR. The 1–563 bp segment of the hybrid promoter (1113 bp long) is derived from GAGαt6E7 plasmid whilst the 564–1113 bp are derived from PCR amplification of Gga plasmid (see below). The 1–115 bp segment of L1 sequence (1503 bp long) is derived from PCR amplification of the pAcC13-6L1 plasmid (Greer et al., *J. Clin. Microbiology*, 2058–2063, 1995 and Munemitsu et al., *Mol. Cell Biol.*, 10:5977–5982, 1990), whilst the 116–1503 bp segment is derived from pAcC13-6L1 plasmid directly. The DNA sequence of HPV 6 is reported in Schwarz et al., *EMBO J.*, 2:2341–2348, 1983.

The GAGαt6E7 plasmid is a derivative of pGEM-3z (Promega) vector in which the following sequence was constructed (from 5' to 3'): ADH2\GAP promoter, an α-factor derived leader sequence, and the HPV-6E7 coding sequence. The GAGαt6E7 plasmid was digested with Bcl I and Xba I. The DH5α derived plasmid DNA could not be cut with Bcl because the DH5α cells are dam+, but the Bcl I enzyme is inhibited by overlapping dam methylation; in order to obtain a Bcl I digestible DNA the plasmid was transformed in the dam-JM110 *E. coli* cells (Stratagene). The JM110 derived plasmid was digested with Bcl I and Xba I, the fragment containing the vector and the 5' half of the ADH2\GAP promoter was gel purified and set aside for further ligation.

The pAcC13-6L1 plasmid was digested with Xba I the insert was gel purified and set aside for ligation. The Xba I insert consisted in the L1 sequence from bp 115 to the end of the sequence, including the stop codon.

The recombinant PCR is schematically represented in FIG. 2. The sequences of the primers are listed below.

```
RP5 5'-ACTGATAGTTTGATCAAAGGGGCAAAACGTAGGGGC-3'    SEQ ID NO:1

RP6 5'-GTCGCTAGGCCGCCACATGGTGTTTGTTTATGTGTG-3'    SEQ ID NO:2

RP7 5'-AAACACACATAAACAAACACCATGTGGCGGCCTAGC-3'    SEQ ID NO:3

RP8 5'-GCAGTCACCACCCTGTACAGGTGTATTAGTACACTG-3'    SEQ ID NO:4
```

A first PCR was performed using the RP5 and RP6 primers and the Gga plasmid DNA as template. The Gga plasmid is a pGEM-3z plasmid derivative obtained in the context of the previous procedures for the HPV-6E7 cloning in yeast and contains the ADH2\GAP promoter. The goal of this first PCR was to obtain the 563–1113 bp portion (3' half) of the ADH2\GAP promoter. The RP5 primer overlapped a Bcl I site. A second PCR was performed using the RP7 and RP8 primers and the pAcC6L1 (Greer et al., 1995) plasmid as template. The goal of this second PCR was to amplify the 5' end of the L1 sequence from the initiation codon to the bp 543. The amplified fragment would contain an Xba I site at position 115. The RP6 and RP7 primers were designed in such a way that the 3' end of the first PCR product would anneal to the 5' end of the second PCR product A third PCR was performed by mixing the first and second amplimers and the eternal primers RP5 and RP8. During this PCR a joining between first and second amplimers would happen and also an amplification of the joined product.

The expected 1126 bp product of the third PCR was predicted to consist in the 563–1113 (3' half) sequence of the ADH2\GAP promoter joined to the 1–530 (5' end) sequence of the HPV-6L1 ORF. The final PCR product would have a Bcl I site at the 5' end and an Xba I site in the L1 portion of the sequence at position 115. The third PCR product was digested with Bcl I and Xba I and gel purified The fragment containing the pGEM-3z vector and the 5' half of the promoter coming from the Bcl I-Xba I digestion of the GAGαt6E7 plasmid was limited with the Bcl I-Xba I digested recombinant PCR product and to the L1 insert coming from the Xba I digestion of pAc13-6L1 plasmid.

After transformation into DH5α cells, several transformants were obtained. The miniprep DNAs from 14 transformants were digested using Eco RI. The Eco RI enzyme was chosen because by using this enzyme it has been possible to verify both the expected molecular sizes and the correct orientation of the 6L1 fragment. The 6L1 fragment had identical extremities (such as Xba I), therefore the probability for the fragment to assume an opposite orientation was 50%. By using Eco RI the plasmid DNA of the right clones should give two fragments, 2600 and 2700 bp long The miniprep DNA of the no. 8 clone gave a single band on a first gel but by running the gel much more was possible to resolve the 2600 and 2700 bp fragments. Also using Sph I it was possible to have a further indication that the clone no. 8 was good. It was, thus, assumed that the clone no. 8 contained the correct pGAG-6L1 plasmid consisting in the pGEM-3z vector containing the HPV-6 L1 sequence under the control of the ADH2\GAP promoter.

The ADH2\GAP-HPV-6L 1 insert was excised from pGAG-6L1 plasmid by digesting with Bam HI and Sal L the insert was gel purified and set aside for further ligation. The promoter-L1 fragment and the pBS24.1 vector were ligated and the product of the reaction was transformed into DH5α cells. The miniprep DNAs from 5 transformants were analyzed by digesting the Bam HI and Sal I and the clones A, B, C, and E were selected as good clones exhibiting the right molecular weight pattern.

A clone was transformed in JSC310 strain of *Saccharomyces cerevisiae* by means of electroporation and the cells were plated on URA-plates. Selected transformants were picked from URA-plates and streaked on LEU-plates. Single colonies from LEU-plates were inoculated in LEU-medium. Four clones grown in LEU-medium were reinoculated in YEPD medium. Cell pellets from the four JSC310-6L1 clones, A, B, C and D were frozen at −20° C. after 24 and 48 hours of growth in YEPD medium on purpose to check L1 protein expression Glycerol batches of the four clones were stored at −80° C.

The 6L1 yeast cell pellets were glass beads extracted, soluble and insoluble extras were separated by means of centrifugation and prepared for SDS-PAGE analysis. Extracts from a strain not containing the pBS-6L1 plasmid (JSC310 cells transformed with pAB24 vector) were also prepared a negative control. In Coomassie strained gel and in western immunoblot an induced band exhibiting the expected molecular weight was visible A comparison of the HPV-6L1 expressed in the yeast JSC310 strain and the same antigen expressed in insect cells showed that the two antigens have similar molecular weight.

The DNA portion of the L1 gene deriving from recombinant PCR (bp 1–115) has been sequenced using the following primer:

5' TAGTTTTAAAACACCAA 3' SEQ ID NO:12.

The primer annealed at the 3' end of the ADH2\GAP promoter, at position −37 from the L1 start codon. The pGAG-6L1 plasmid (pGEM-3z containing the ADH2\GAP promoter fused to the L1 sequence) was used as template. By sequencing it was established that no errors occurred during the recombinant PCR manipulations nor in the cloning steps.

To construct the YIpAde integrative plasmid, a 1,059 bp XbaI genomic DNA fragment of the *S. cerevisiae* adenine 2 gene (Ade2) was amplified by using the PCR oligonucleotide primers 5'-AdeE (5'-GCGGC GAATTCTAGAACAGTTGGTATATTAG-3' SEQ ID NO:5, inserting an EcoRI site) and 3'AdeP (5'GCGGC CTGCAGGGTCTAGACTCTTTTCCATATA-3'SEQ ID NO:6, inserting PstI site). The amplified DNA fragment was cloned into plasmid pUC8 digested with EcoRI and PstI and the XbaI sites, included in the amplified DNA fragment, were used to excise the insert for yeast transformation. To obtain the integrative YIpLys-L2 expression plasmids, a 1,318 bp genomic DNA fragment of the *S. cerevisiae* lysine 2 (Lys2) gene was amplified by using the PCR oligonucleotide primers 5'LysE (5'-GCG GAATTCCACTAGTAATTACA-3'SEQ ID NO:7, inserting an EcoRI site) and 3'LysH (5'-GATGT AAGCTTCTACTAGTTGA-3'SEQ ID NO:8, inserting a HindIII site). The amplified DNA fragment was then inserted into pUC8 (derivatives readily available from commercial sources, e.g., Promega) digested with EcoRI and HindIII generating a plasmid named YIpLys. A BamHI DNA fragment from pSI3 vector (Isabel Zaror, Chiron Corporation, Emeryville, Calif., USA, pBR322 backbone, ADH2/GAP promoter, SOD protein, and $T_{MF\alpha}$) including the ADH2/GAP promoter, the human superoxide dismutase (SOD) gene and the $T_{MF\alpha}$ transcriptional termination sequence, was cloned into the single BglII restriction site in the Lys2 gene sequence of YIpLys, obtaining a plasmid named YIpLys-SOD. The YIpLys-6L2 plasmid was derived from YIpLys-SOD replacing the NcoI-SalI DNA fragment encoding the SOD gene with the NcoI-SalI DNA fragment from pGEM3z-6L2 (Kent Thudium, Chiron Corporation, Emeryville, Calif., USA) encoding the PV-6b L2 open reading frame (ORF). To construct the YIpLys-16L2 plasmid, the L2 gene was amplified from the cloned HPV-16 genomic DNA (kindly provided in this instance by Dennis J. McCance, University of Rochester, N.Y.) by using the PCR oligonucleotide primers DT-5'L2 (5'-CGACACAAACGT-TCTGCAA-3'SEQ ID NO:9) and DT-3'L2 (5'-ATTA GTCGACCTAGGCAGCCAAGAGACATC-3'SEQ ID NO:10), including the translation termination codon and a SalI site. The DNA fragment obtained was digested with SalI and cloned into YIpLys-SOD from which the SOD coding sequence had been removed by digestion with NcoI filling-in with Klenow enzyme and digestion with SalI.

The pBS-6L2 and pBS-16L2 episomal expression plasmids were obtained by replacing a SacI-SalI DNA fragment from pBS-6L1, including part of the ADH2/GAP promoter and the entire HPV6b L1 ORF; with SacI-SalI DNA fragments, derived from either YIpLys-6L2 or YIpLys-16L2, including the corresponding promoter region and the L2 ORF.

To construct the pBS-16L1 episomal expression plasmid, the L1 gene was amplified from cloned HPV-16 genomic DNA by using the PCR oligonucleotide primers DT-5'L1 (5'-TCTCTTGGCTGCCTAGTGAGGCCA-3' SEQ ID NO:11) and DT-3'L1 (5'-CTAGTAAT GTCCACTTACAGCTTACGTTTTTTGCG-3'SEQ ID NO:12, comprising the translational termination codon and a SalI site. The amplified DNA fragment was purified from agarose gel and cloned into blunt-ended pSI3 vector from which the SOD gene had been previously removed by digestion with NcoI and SalI restriction enzymes and filling-in with Klenow enzyme. From this intermediate construct, a SacI-SalI DNA fragment, including part of the ADH2/GAP promoter and the HPV-16L1 ORF, was purified and used to replace the corresponding SacI-SalI DNA fragment in pBS-6L1.

EXAMPLE 3

Generation of Recombinant Yeast Strains

The strains JSC310-6L1epi (14), JSC310-16L1epi JSC310-6L2epi and JSC310-16L2epi expressing the four capsid proteins by means of episomal vectors, were obtained by transformation of the parental JSC310 strain with the expression plasmids pBS-6L1 (14), pBS-16L1, pBS-6L2 and pBS-16L2.

The JSC310-6L2int and the AB110-16L2int strains were obtained using the following experimental approach. Competent yeast cells were cotransformed with 5 µg of EcoRI-HindIII digested YIpLys-6L2 or YIpLys-16L2 integrative plasmid and 1 µg of pBS24.1 episomal vector to allow the selection of transformants. Different clones were tested for growth onto plates of minimal medium (MM) supplemented with α-adipate to select mutants with an inactivated Lys2 gene (49). Correct integration into the lys2 locus was verified by PCR analysis by using pairs of oligonucleotide primers complementary to sequences within the expression cassette and the genomic portion of the Lys2 gene. Among the colonies expressing the L2 protein, one was chosen, cured of the pBS24.1 plasmid and tested for the inability to grow in the absence of uracil and leucine introduction of the episomal L1 expressing vectors into these strains was carried out following two differ strategies. AB110-16L2int was transformed with the pBS-6L1 expression plasmid and selection of transformants on MM plats without leucine and uracil allowed the isolation of the haploid strain AB110-6L1/16L2. The JSC310-6L2int strain was instead cotransformed with the pBS-16L expression vector and with the XbaI digested YIpAde investigative plasmid. Transformants grown on selective plates were plated on complete yeast extract-peptone medium (YEP) and allowed to grow at 30° C. for 3–4 days until colonies (1–2%) developed a red color due to disruption of the ade2 locus (52). One of the clones, which showed correct integration into the ade2 locus by PCR and L1 and L2 expression by Western blot analysis, was designated JSC310-16L1/6L2.

Generation of the AB/JSC-4L diploid strain was obtained by mixing cultures, in YEP medium containing 5% glucose, of the two haploid strains, AB110-6L/16L2 and JSC310-16L1/6L2. Selection of the AB/JSC-4L diploid strain required an additional genetic marker in the haploid JSC310-6L2int strain. This was obtained inactivating the endogenous Ade2 gene by means of the integration plasmid represented in FIG. 4a Diploid cells were selected onto MM plates lacking histidine and adenine.

Expression of the four proteins in the haploid strains and in the strain resulting from their mating was evaluated by Western blot analysis. FIG. 5 shows the results of such experiments demonstrating that both the haploid strains AB110-6L1/16L2 (a and d, lanes 1) and JSC310-16L1/6L2 (b and c, lanes 2) expressed the heterologous genes and that the expression of all four proteins was stably maintained in the resulting AB/JS-4L diploid strain (a, b, c and d, lanes 3).

EXAMPLE 4

Preparation of VLPs

Parental yeast strains were grown in complete YEP medium. Strains transformed with episomal vectors were first cultured in leucine-deficient MM medium with 4% glucose until they reached midlog phase. Expression of the genes under the control of the ADH2/GAP glucose-repressible promoter was induced by diluting these culture 1:50 into YEP complete medium and culturing the cells at 30° C. for 2–3 days. Total cell extract were prepared from 3.5 optical densities (OD) of yeast cell cultures go to approximately $OD_{600}$ =20. Cells were lysed with a 10 minute incubation on ice in 024 N NaOH and 0.96% β-mercaptoethanol, followed by trichloracetic acid (TCA) precipitation, ice cold acetone washing and final suspension of the protein pellet in 100 µl of protein loading buffer. To carry out dot-blot experiments where preservation of L1 conformation was necessary, yeast cells were collected, washed, suspended in phosphate-buffered saline (PBS, pH 7.5) and disrupted by vortexing five times for 1 minute in the presence of glass beads (425–600 µm, Sigma).

Frozen yeast cell pellets were thawed in buffer containing 0.1 M Tris-HCl (pH 7.5)10.15 M NaCl 2 mM $MgCl_2$ and 1 mM EGTA (#E3889, Sigma Chemical Co.) and Complete™ Protease Inhibitors (#1-697-498, Boehringer Mannheim). Cells were disrupted by vortexing twice for 10 minutes with a 5 minute interval on ice, in the presence of glass beads (0.5 ml beads per ml of cell suspension) using a VWRbrand Multi-tube vortexer (VWR Scientific Product). Cellular debris was removed by a 20 minute centrifugation at 2000× g. The supernatants were then centriged through a 40% (w/w) sucrose cushion (2 hour centrifugation at 100,000×g). The resulting pellets were suspended in PBS, applied to a pre-formed CsCl gradient (1.17–1.57 g/ml) and centrifuged for 24 hours at 285,000×g. The gradients were fractionated and aliquots from each fraction were subjected to Western blot analysis with type-specific anti-L1 and anti-L2 antibodies. Peak fractions were pooled and dialyzed against PBS. Total protein concentration was determined by BCA™ Protein Assay Reagent (#23225, Pierce Chemicals).

EXAMPLE 5

Characterization of VLPs

Proteins were analyzed by denaturing sodium-dodecyl sulfate polyacrylamide gel electrophoresis (SDS-PAGE, 10% polyacrylamide) and Western blotting onto nitrocellulose membrane (pore size 0.45 µm, MSI, Westborough, MA USA) according to standard protocols. Dot-blot analysis of denatured and reduced VLPs was carried out boiling the protein samples for 5 minutes in the presence of dithiothreitol (DTI) before applying them to nitrocellulose filters using a bio-dot apparatus (Biorad). When native VLP structure had to be maintained, VLPs in PBS were applied to the membrane without boiling and in the absence of DTT. Reaction with HPV-specific antibodies was detected using the Enhanced Chemiluminescence (ECL) Western blotting reagent (Amersham) and Hyperfilm ECL (Amersham).

Figure 6A:
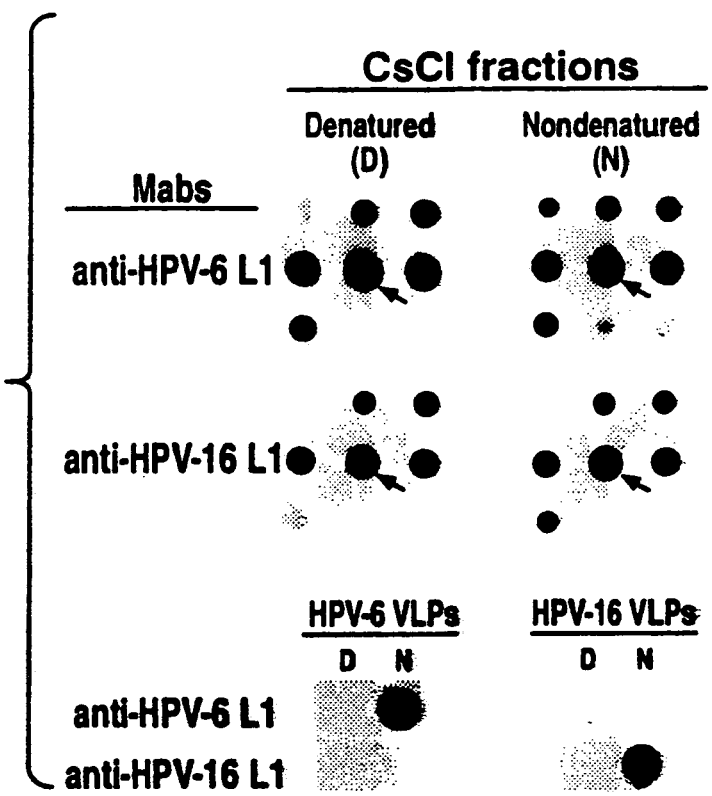
FIG. 6 depicts an analysis of fractions from CsCl gradient sedimentation of AB/JS-4L cell extract. (A) Aliquots from fractions 1 to 9 were blotted onto nitrocellulose filters using either (a and c) denaturing and reducing (D) or (b and d) nondenaturing and nonreducing (N) conditions. The filters were incubated with the type-specific anti-L1 H6.C6 (a) and H16.H5 (c) Mabs, and with the conformationally dependent type-specific anti-L1 H6.B10.5 (b) and H16.V5 (d) Mabs. As a control, the anti-HPV-6 and HPV-16 L1 conformational Mabs were incubated with CsCl purified VLPs (e) blotted under either denaturing or nondenaturing conditions. The arrows in A indicate fraction no. 5. (B) Aliquots of faction no. 5 were subjected to SDS-PAGE, electroblotted on nitrocellulose filters and incubated either with HPV-6 L2 (lane 3a) or HPV-16 L2 (lane 3b) antiserum. As a control, total cell extracts from the JSC310-6L2epi (lanes 1) and JSC310-16L2epi (lanes 2) strains were used. Molecular mass standards (in kDa) are indicated. Arrows indicate bands corresponding to the L2 proteins.
Figure 6B:
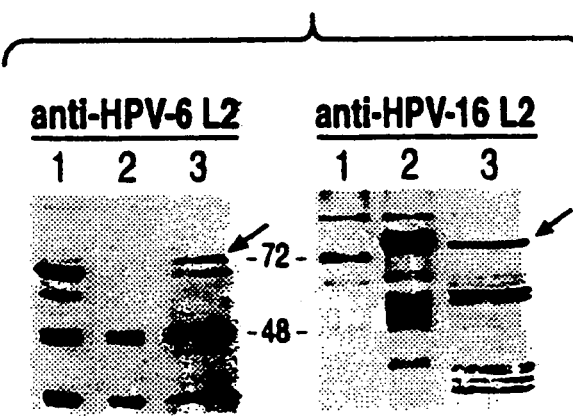
Figure 7A:
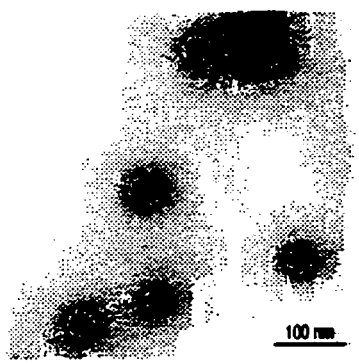
FIG. 7 depicts an electron microscope (EM) analysis of CsCl purified VLPs. HPV-6 (a), HPV-16 (b) and HPV-6/16 VLPs were adsorbed onto Formvar-carbon coated grids, stained with 4% uranyl acetate and examined under a Zeiss EM10C microscope at a magnification of ×100,000 (Bar-100 nm).
Figure 7B:
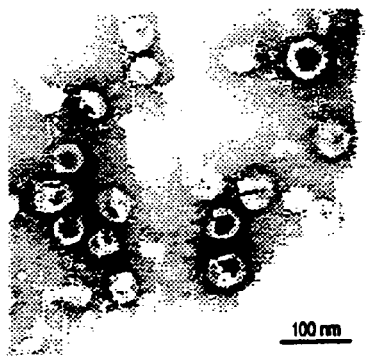
Figure 7C:
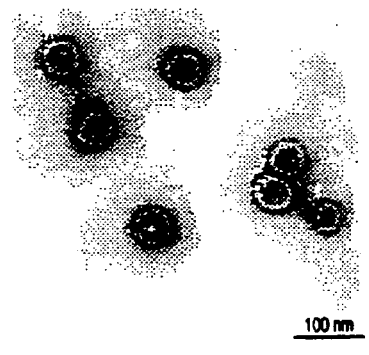

Specifically, the cell extract from the diploid strain was subjected to CsCl gradient sedimentation and aliquots of the collected fractions were boiled in the presence of DTT and blotted in duplicate onto nitrocellulose filters. The filters were incubated with anti-HPV-6 and anti-HPV-16 specific Mabs which react with denatured L1 (8,9), revealing that the two L1 proteins were enriched in the same fractions (FIG. 6A, a and c). The dot-blot experiment was repeated without denaturing and without reducing the protein samples and using anti-HPV-6 and HPV-16 L1 specific Mabs which were previously reported to react exclusively with intact VLPs in enzyme-linked immunosorbent assay (ELISA) experiments (8, 9). The result obtained confirmed that the two conformationally dependent Mabs were able to recognize the L1 proteins which copurified in the CsCl fractions (FIG. 6A, b and d). As expected, the two Mabs reacted specifically with HPV-6 and HPV-16 control VLPs only under nondenaturing and nonreducing conditions (FIG. 6A, e). Western blot analysis of fraction 5 confirmed that both HPV-6 and HPV-16 L2 proteins were also present (FIG. 6B, a and b). Estimation of the refractive index of the identified protein peak gave a value of 1.29–1.3 mg/ml. EM analysis of the enriched fraction revealed the presence of VLPs which appeared to be similar to control VLPs formed by either HPV-6 or HPV-16 L1 (FIG. 7).

Figure 8A:
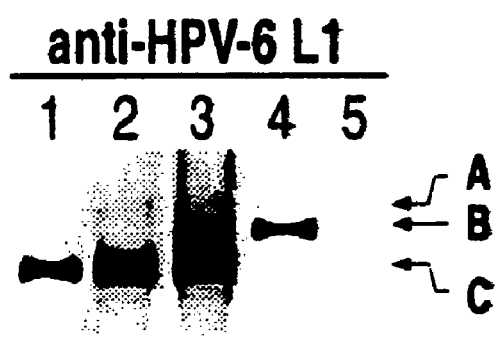
FIG. 8 depicts a Western blot analysis of immunoprecipitated VLPs. CsCl banded VLPs from the AB/JS-4L diploid strain were immunoprecipitated with the anti-HPV-6 L1 conformationally dependent H6.B10.5 Mab. The immunoprecipitated proteins were separated using a 15 centimeter (cm) long 10% polyacrylamide SDS-gel, electroblotted on nitrocellulose membrane and incubated either with the anti-HPV6 L1 specific H6.C6 Mab (a) or with the anti-HPV-16 L1 specific H16.H5 Mab (b). Control reactions, including either VLPs or the conformational Mab only, were setup and processed under identical experimental conditions. Lane 1: VLPs incubated overnight without the Mab; lane 2: Mab incubated overnight; lane 3: VLPs incubated overnight with the H6.B10.5 conformational Mab; lane 4: total cell extract from the JSC310-6L1 epi strain; lane 5: total cell extract from the JSC310-16L1epi strain. Arrows indicate a conformational Mab-derived band (A), the L1 bands (B) and a protein A Sepharose-derived band (C).
Figure 8B:
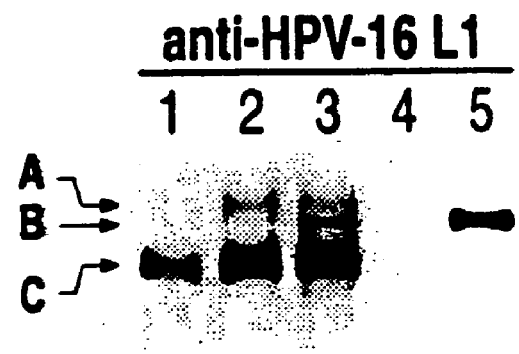

To evaluate whether the HPV-6 and HPV-16 L1 proteins could interact and assemble into mosaic VLPs, we performed immunoprecipitation experiments using CsCl banded VLPs and the specific anti-HPV-6 L1 conformationally dependent Mab H6.B10.5 (9). Approximately 1 µg of CsCL banded VLPs were diluted with PBS and incubated with the conformationally dependent anti-PV-6 L1 Mab H6B10.5 (1:1000 dilution) overnight at 4° C. with gentle shaking. The immune complexes were collected with Protein A Sepharose CL-4B (Pharmacia Biotech), washed 4 times with 1 ml PBS, suspended in sample buffer, boiled for 5 minutes, subjected to SDS-PAGE and analyzed by Western blot using anti-HPV-6 and anti-HPV-16 L1 Mabs. The Western blot carried out on the immunoprecipitates using specific anti-L1 Mabs (FIG. 8) identified three major bands: (A) was a Mab-derived band, since it could be also observed when the conformational Mab was immunoblotted with the anti-mouse antibody, (B) was a band that appeared only when the VLPs were incubated with the conformational anti-PV-6 L1 Mab (lanes 3), identifying specifically immunoprecipitated proteins with an eletrophoretic mobility corresponding to that of HPV-6 L1 (a, lane 4) and HPV-16 L1 (b, lane 5); (C) was a resin-derived band that was also detected when an aliquot of protein A Sepharose was suspended in PBS and immunoblotted with the anti-mouse antibody. Bands (B) were not visible when the immunoprecipitation was carried out using an unrelated Mab Similarly, HPV-16 L1 could not be detected when HPV-6 and HPV-16 VLPs were mixed and immunoprecipitated.

EXAMPLE 6

Mouse Immunization with VLPs.

To investigate whether HPV-6/16 mosaic VLPs were able to induce an immune response directed against both HPV types, groups of mice were immunized subcutaneously with HPV-6, HPV-16 and mosaic VLPs and the sera were tested after the third immunization. Six week old female Balb/c mice were injected subcutaneously with 20 µg of the following purified antigens: (I) HPV-6 VLPs, (ii) HPV-16 VLPs, (iii) HPV-6/16 VLPs. All the antigens were administered with equal volume of MF59 adjuvant (30). A group of control mice was injected only with MF59. The mice were boosted with 15 µg of the respective antigen at week 3 and 10 µg at week 5. Serum samples were collected on day 12 after the final booster and assayed for capsid protein specific antibodies.

Figures 9A, 9B:
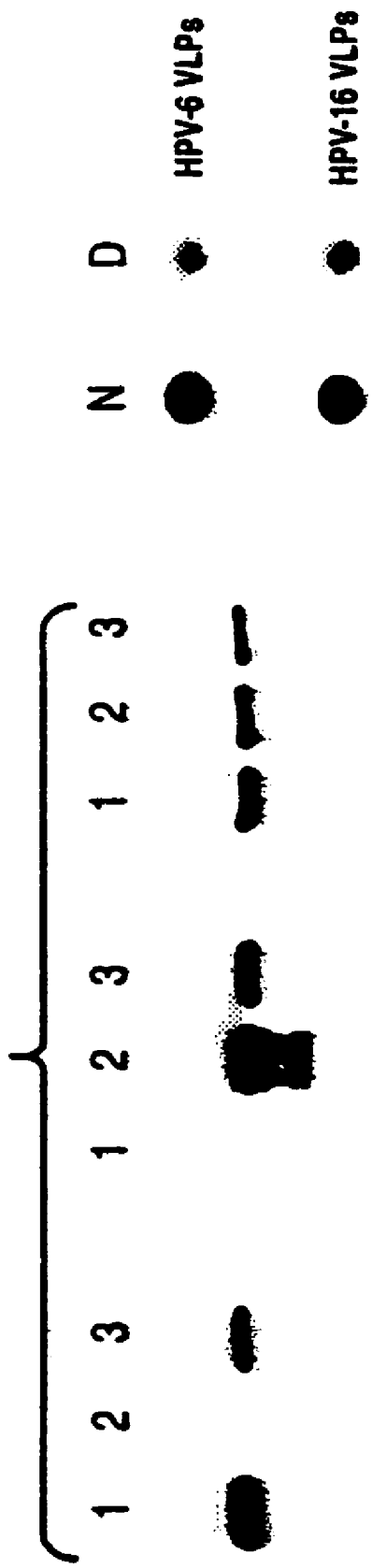
FIG. 9 depicts a characterization of sera derived from mice immunized with HPV-6, HPV-16 and mosaic VLPs. (A) Comparable amounts of HPV-6 (lanes 1), HPV-16 (lanes 2) and mosaic VLPs (lanes 3) were separated on SDS-PAGE and immunoblotted with antisera from mice immunized with HPV6 VLPs (a) HPV-16 VLPs b) and mosaic VLPs (c). (B) Comparable amounts of HPV6 and HPV-16 VLPs were dot-blotted under denaturing and reducing (D) and nondenaturing and nonreducing (N) conditions and incubated with the S16 antiserum of a mice immunized with mosaic VLPs.

FIG. 9A shows the result of the Western blot carried out with the three types of denatured VLPs incubated with three sera, each representative of the different groups of immunized mice. While the reactivity of the sera from mice immunized either with HPV-6 or HPV-16 VLPs was predominantly type-specific (FIG. 9A, a and b), the serum from mouse 16 (S16), immunized with HPV6/16 VLPs, reacted against both HPV-6 and HPV-16 L1 (FIG. 9A, c). To analyze whether the immune response was also directed against conformational epitopes of the L1 proteins, equal amounts of either HPV-6 or HPV-16 VLPs were blotted under dang and nondenaturing conditions and incubated with the S16 antiserum FIG. 9B shows that the signal was significantly lower when the samples were denet and reduced, suggesting that conformational antibodies had been elicited.

The foregoing examples are meant to illustrate the invention and are not to be construed to limit the invention in any way. Those skilled in the art will recognize modifications that are within the spirit and scope of the invention. All references cited herein are hereby incorporated by reference in their entirety.

REFERENCES

1. Bonnez, W., R. C. Rose, C. da Rin, C. Borkhuis, K. de Mesy Jensen, and R. C. Reichman. 1993. Propagation of human papillomavirus type 11 in human xenografts using the severe combined immunodeficiency (SCID) mouse and comparison to the nude mouse model. Virology 197:455–458.
2. Bonnez; W., C. da Rin, C. Borkhuis, K. de Mesy Jensen, R. C. Reichman, and R. C. Rose. 1998. Isolation and propagation of human papillomavirus type 16 in human xenografts implanted in the severe combined immunodeficiency mouse. J. Virol. 72:5256–5261.
3. Chan, S. Y., H. U. Bernard, C. K. Hong, S. P. Chan, B. Hoffmann, and H. Delis. 1992. Phylogenetic analysis of 48 papillomavirus types and 28 subtypes and variants: a showcase for the molecular evolution of DNA viruses. J. Virol. 66:5714–5725
4. Chang, C, S. Zhou, D. Ganem, and D. N. Standring. 1994. Phenotypic mixing between different hepadnavirus nucleocapsid proteins reveals C protein dimerization to be cis preferential. J. Virol. 68:5225–5231.
5. Christensen, N. D., and J. W. Kreider. 1990. Antibody-mediated neutralization in vivo of infectious papillomavirus. J. Virol. 64:3151–3156.
6. Christensen, N. D., J. W. Kreider, N. M. Cladel, S. D. Patrick, and P. A. Welsh. 1990. Monoclonal antibody-mediated neutralization of infectious human papillomavirus type 11. J. Virol. 64:5678–5681.
7. Christensen, N. D., R. Kirnbauer, J. T. Schiller, S. J. Ghim, R. Schlegel, and J. W. Kreider. 1994. Human papillomavirus types 6 and 11 have antigenically distinct strongly immunogenic conformationally dependent neutralizing epitopes. Virology 205:329–335.

8. Christensen, N. D., C. A. Reed, N. M. Cladel, K. Hall, and G. S. Leiserowitz. 1996. Monoclonal antibodies to HPV-6 L1 virus-like particles identify conformational and linear neutralizing epitopes on HPV-11 in addition to type-specific epitopes on HPV-6. Virology 224:477–486.

9. Christensen, N. D, J. Dillner, C. Eklund, J. J. Carter, G. C. Wipf, C. A. Reed, N. M. Cladel, and D. A. Galloway. 1996. Surface conformational and linear epitopes on HPV-16 and HPV-18 L1 virus-like particles as defined by monoclonal antibodies. Virology 223:174–184.

10. Deminie, C. A., and M. Emerman. 1993. Incorporation of human immunodeficiency virus type 1 Gag proteins into murine leukemia virus virions. J. Virol. 67:6499–6506.

11. Doorbar, J., and P. H. Gallimore. 1987. Identification of proteins encoded by the L1 and L2 open reading frames of human papillomavirus 1a J. Virol. 61:1131–1142.

12. Firziaff, J. M., N. B. Kiviat, A. M. Beckmann, S. A. Jenison, and D. A. Galloway. 1988. Detection of human papillomavirus capsid antigens in various squamous epithelial lesions using antibodies directed against the L1 and L2 open reading frames. Virology 164:467–477.

13. Franke, E. K., H. E. H. Yuan, K. L. Bossolt, S. P. Goff, and J. Luban. 1994. Specificity and sequence requirements for interactions between various retroviral Gag proteins. J. Virol. 68:5300–5305.

14. Greer K. E., R. Petracca, B. Gervase, D. Tornese Buonamassa, M. Ugozzoli, A. Di Tommaso, M. T. De Magistris, G. Van Nest, and G. Bensi. in preparation.

15. Hagensee, M. E., N. Yaegashi, and D. A. Galloway. 1993. Self-assembly of human papillomavirus type 1 capsids by expression of L1 protein alone or by coexpression of the L1 and L2 capsid proteins. J. Virol. 67:315–322.

16. Hagensee, M. E., N. H. Olson, T. S. Baker, and D. A. Galloway. 1994. Three-dimensional structure of vaccinia virus-produced human papillomavirus type 1 capsids J. Virol. 68:4503–4505.

17. Hines, V., W. Zhang, N. Ramakrishna, J. Styles, P. Mehta, K. S. Kim, M. Innis, and D. L. Miller. 1994. The expression and processing of human beta-amyloid peptide precursors in Saccharomyces cerevisiae: evidence for a novel endopeptidase in the yeast secretory system. Cell. Mol. Biol. Res. 40:273–284.

18. Hofmann, K. J., J. C. Cook, J. G. Joyce, D. R. Brown, L. D. Schultz, H. A. George, M. Rosolowsky, K. H. Fife, and K. U. Jansen. 1995. Sequence determination of human papillomavirus 6a and assembly of virus-like particles in Saccharomyces cerevisiae. Virology 209:506–518.

19. Hofmann, K. J, M. P. Neeper, H. Z. Markus, D. R. Brown, M. Muller, and K. U. Jansen. 1996. Sequence conservation within the major capsid protein of human papillomavirus (HPV) type 18 and formation of PV-18 virus-like particles in Saccharomyces cerevisiae. J. Gen. Virol. 77:465–468.

20. Jansen, K. U., M. Rosolowsky, L. D. Schultz, H. Z. Markus, J. C. Cook, J. J. Donnelly, D. Martinez, R. W. Ellis, and A R. Shaw. 1995. Vaccination with yeast-expressed cottontail rabbit papillomavirus (CRPV) virus-like particles protects rabbits from CRPV-induced papilloma formation. Vaccine 13:1509–1514.

21. Kirnbauer, R, G. Booy, N. Cheng, R. R. Lowy, and J. T. Schiller. 1992. Papillomavirus L1 major capsid protein self-assembles into virus-like particles that are highly immunogenic. Proc. Natl. Acad. Sci. USA 89:12180–12184.

22. Kirnbauer, R, J. Taub, H. Greenstone, R. B. S. Roden, M. Durst, L. Gissmnan, D. R. Lowy, and J. T. Schiller. 1993. Efficient self-assembly of human papillomavirus type 16 L1 and L1-L2 into virus-like particles. J. Virol. 67:6929–6936.

23. Kirnbauer, R., L. M. Chandrachud, B. W. O'Neil, E. R. Wagner, G. J. Grindlay, A. Armstrong, G. M. McGarvie, J. T. Schiller, D. R. Lowy, and M. S. Campo. 1996. Virus-like particles of bovine papillomavirus type 4 in prophylactic and therapeutic immunization. Virology 219:37–44.

24. Kreider, J. W., M. K. Howett, A. E.-Leure-Dupree, R. J. Zaino, and J. A. Weber. 1987. Laboratory production in vivo of infectious human papillomavirus type 11. J. Virol. 61:590–593.

25. Li, T. P. Cripe, P. A. Estes, M. K. Lyon; R. C. Rose, and R. L. Garcea. 1997. Expression of the human papillomavirus type-11 capsid protein in Escherichia coli: characterization on of protein domains involved in DNA-binding and capsid assembly. J. Virol. 71:2988–2995.

26. Li, M., P. Beard, P. A. Estes, M. K. Lyon, and R. L. Garcea. 1998. Intercapsomeric disulfide bonds in papillomavirus assembly and disassembly. J. Virol. 72:216–2167.

27. Lowe, R. S., D. R. Brown, J. T. Bryan, J. C. Cook, H. A. George, K. J. Hofmann, W. M. Hurni, J. G. Joyce, E. D. Lehman, H. Z. Markus, M. P. Neeper, L. D. Schultz, A. R. Shaw, and K. U. Jansen. 1997. Human papillomavirus type 11 (HPV-11) neutralizing antibodies in the serum and genital mucosal secretions of African green monkeys immunized with HPV-11 virus-like particles expressed in yeast. J. Infect. Dis. 176:1141–1145.

28. Muller, M., L. Gissmann, R. J. Cristiano, X. Y. Sun, H. Frazer, A. B. Jenson, A. Alonso, H. Zentgraf, and J. Zhou. 1995. Papillomavirus capsid binding and uptake by cells from different tissues and species. J. Virol. 69:948–954.

29. Neeper, M. P., K. J. Hofmann, and K. U. Jansen. 1996. Expression of the major capsid protein of human papillomavirus type 11 in Saccharomyces cerevisiae. Gene 180:1–6.

30. Ott, G., G. L. Barchfeld, D. Chernoff, R. Radakrishnan, P. van Hoogevest and G. van Nest 1995. MF59: Design and evaluation of a safe and potent adjuvant for human vaccines, p. 277–296. In M. F. Powell and M. J. Newman (ed.), Vaccine design. The subunit and adjuvant approach. Plenum Press, New York, N.Y.

31. Qi, Y. M., S. W. Peng, K. Hengst, M. Evander, D. S. Park, J. Zhou, and I. A. Frazer. 1996. Epithelial cells display separate receptors for papillomavirus VLPs and for soluble L1 capsid protein. Virology 216:35–45.

32. Roden, R. B. E. M. Weissinger, D. W. Henderson, F. Booy, R. Kirnbauer, J. F. Mushinski, D. R. Lowy and J. T. Schiller. 1994. Neutralization of bovine papillomavirus by antibodies to L1 and L2 capsid proteins J. Virol. 68:7570–7574

33. Roden, R. B., R. Kirnbauer, A. B. Jenson, D. R. Lowy, and J. T. Schiller. 1994. Interaction of papillomaviruses with the cell surface J. Virol. 68:7260–7266.

34. Roden, R. B. S., H. L. Greenstone, R. Kirnbauer, F. P. Booy, J. Jessie, D. R. Lowy, and J. T. Schiller. 1996. In vitro generation and type-specific neutralization of human papillomavirus type 16 virion pseudotype. J. Virol. 70:5875–5883.

35. Roden, R. B. S., N. L. Hubbert, R. Kirnbauer, N. D. Christensen, D. R. Lowy, and J. T. Schiller. 1996. Assessment of serological relatedness of genital human papillomaviruses by hemagglutination inhibition. J. Virol. 70:3298–3301.
36. Rose, R. C., W. Bonnez, C. da Rin, D. J. McCance, and R. C. Reichman. 1994. Serological differentiation of human papillomavirus types 11, 16 and 18 using recombinant virus-like particles. J. Gen. Virol. 75:2445–2449.
37. Rose, R. C., W. Bonnez, R. C. Reichman, and R. L. Garcea. 1993. Expression of human papillomavirus type 11 L1 protein in insects cells: in vivo and in vitro assembly of virus-like particles. J. Virol. 67:1936–1944.
38. Sapp, M., C. Volpers, M. Muller, and R. E. Streeck. 1995. Organization of the major and minor capsid proteins in human papillomavirus type 33 virus-like particles. J. Gen. Virol. 76:2407–2412.
39. Sapp, M., C. Fligge, L. Petzak, J. R. Harris, and R. E. Streeck. 1998. Papillomavirus assembly requires trimerization of the major capsid protein by disulfides between two highly conserved cysteines. J. Virol. 72:6186–6189.
40. Smith, L. H., C. Foster, M. E. Hitchcock, G. S. Leiserowitz, K. Hall, R. Iseroff, N. D. Christensen, and J. W. Kreider. 1995. Titration of HPV-11 infectivity and antibody neutralization can be measured in vitro. J. Invest. Dermatol. 105:1–7.
41. Suzich, J. A, S. Ghim, F. J. Palmer-Hill, W. L. White, J. K. Tamura, J. A. Bell, J. A. Newsome, A. Bennet Jenson, and R. Schlegel 1995. Systemic immunization with papillomavirus L1 protein completely prevents the development of viral mucosal papillomas. Proc. Natl. Acad. Sci. USA 92:1553–11557.
42. Touzé, A., C. Dupay, D. Mahé, P. Y. Sizaret, and P. Coursaget. 1998. Production of recombinant virus-like particles from human papillomavirus type 6 and 11, and study of serological reactivities between HPV 6, 11 and 45 by ELISA: implications for papillomavirus prevention and detection. FEMS Microbiol. 160: 111–118.
43. Travis, J., M. Owen, P. George, R. Carrel, S. Rosenberg, R. A. Hallewell, and P. J. Barr. 1985. Isolation and properties of recombinant DNA produced variants of human $\alpha_1$-proteinase inhibitor. J. Biol. Chem. 260:4384–4389.
44. Unckell, F., R. E. Streeck, and M. Sapp. 1997. Generation and neutralization of pseudovirions of human papillomavirus type 33. J. Virol. 71:2934–2939.
45. Van Ranst, M., J. B. Kaplan, and R. D. Burk. 1992. Phylogenetic classification of human papillomaviruses: correlation with clinical manifestations. J. Gen. Virol. 73:2653–2660.
46. Volpers, C., P. Schirmacher, R. E. Streeck, and M. Sapp. 1994. Assembly of the major and the minor capsid protein of human papillomavirus type 33 into virus-like particles and tubular structures in insect cells. Virology 200:504–512.
47. Volpers, C., F. Unckell, P. Schirmacher, R. E. Streeck, and M. Sapp. 1995. Binding and internalization of human papillomavirus type 33 virus-like particles by eukaryotic cells. J. Virol. 69:3258–3264.
48. White, W. L., S. D. Wilson, W. Bon, R. C. Rose, S. Koenig, and J. A. Suzich. 1998. In vitro infection of type-restricted antibody-mediated neutralization of authentic human papillomavirus type 16. J. Virol. 72:959–964.
49. Zaret, K. S., and F. Sherman. 1985. α-Aminoadipate as a primary nitrogen source for *Saccharomyces cerevisiae* mutants. J. Bacteriol. 162:579–583.
50. Zàvada, J. 1982. The pseudotypic paradox J. Gen. Virol. 63:15–24.
51. Zhou J., D. J. Stenzel, X. Y. Sun, and I. H. Frazer. 1993. Synthesis and assembly of infectious bovine papillomavirus particles in vitro. J. Gen. Virol. 74:763–768.
52. Zimmermann, F. K. 1975. Procedures used in the induction of mitotic recombination and mutation in the yeast *Saccharomyces cerevisiae*. Mutat. Res. 31:71–86.

What is claimed is:

1. A virus-like particle (VLP) comprising a first late 1 (L1) capsid protein from human papilloma virus (HPV) type 6 and a second L1 capsid protein from HPV type 16.

2. The VLP of claim 1, further comprising an L2 capsid protein.

3. A composition comprising the VLP of claim 1.

4. The composition of claim 3 wherein the VLP is purified for immunization.

5. The composition of claim 4, wherein the VLP comprises an L2 capsid protein.

6. The composition of claim 5, further comprising an adjuvant.

7. The composition of claim 6 wherein the adjuvant is MF59.

8. The VLP of claim 1 wherein said VLP induces an immune response against both types of viruses.

9. A composition comprising the VLP of claim 8.

10. A method for producing the VLP of claim 1, said method comprising a) cloning said capsid proteins into expression cassettes comprising the same promoters and termination sequences; and b) expressing said cassettes in the same yeast diploid host cell.

11. The method of claim 10 wherein the yeast is Saccharomyces cerevisiae.

12. The method of claim 10, wherein the capsid proteins further comprise L2 capsid proteins.

13. The method of claim 12 wherein said L1 protein expression cassettes are cloned into non-integrative vectors, and said L2 proteins expression cassettes are cloned into integrative vectors.

14. The method of claim 13 wherein the non-integrative vector is pBS24.1.

15. The method of claim 13 wherein the integrative vector is pUC8.

16. A method for inducing an immune response against more than one type of virus comprising administering the VLP of claim 1.

17. A method for inducing an immune response against more than one type of virus comprising administering the composition of claim 5.

* * * * *